United States Patent [19]

Norell

[11] 3,965,132

[45] June 22, 1976

[54] ACID AND ESTER PRODUCTION
[75] Inventor: John R. Norell, Bartlesville, Okla.
[73] Assignee: Phillips Petroleum Company, Bartlesville, Okla.
[22] Filed: June 3, 1974
[21] Appl. No.: 475,977

[52] U.S. Cl........................... 260/410.9 R; 260/413; 260/468 G; 260/497 R; 260/514 G; 260/533 R
[51] Int. Cl.².................... C07C 51/14; C07C 67/38
[58] Field of Search....... 260/468 G, 468 M, 514 G, 260/514 M, 413, 410.9 N,

[56] References Cited
UNITED STATES PATENTS
3,282,973  11/1960  Devine et al........................ 260/413

FOREIGN PATENTS OR APPLICATIONS
2,241,807  3/1973  Germany............................ 260/468

Primary Examiner—Robert Gerstl

[57] ABSTRACT

Acids containing $2n+1$ carbon atoms and esters containing $[(2n+1) + n']$ carbon atoms are produced, respectively, by the reaction of olefins containing $n$ carbon atoms with carbon monoxide and water or alcohols containing $n'$ carbon atoms in the presence of trifluoromethanesulfonic acid. The carbon number of esters from diols is given by $[2(2n+1) + n']$ wherein $n'$ represents the carbon number of the diol.

10 Claims, No Drawings

ACID AND ESTER PRODUCTION

For convenience herein, the acid products are also referred to as "dimer acids." Alternatively, esters are produced by substitution of alcohols for water. For convenience, such esters are also referred to herein as "dimer esters." The carbon numbers of such esters, of course, are defined by [(2n+1) + n'] wherein n represents the number of carbons in the olefine and n' represents the carbon number of the alcohol used to produce the ester. The carbon number of esters from diols is given by [2(2n+1) + n'] wherein n and n' are as defined above.

It is an object of this invention to provide a new process for the production of acids.

Another object of this invention to provide a new process for preparing esters.

In accordance with another object of this invention, there is provided a catalyst effective for the production of acids and esters.

Another object of this invention is to provide an improved process for the production of acids and esters from olefinic feeds at low costs and at high yields.

A further object of this invention is to provide an improved process for the production of acids and esters from olefinic feeds with minimum byproduct formation.

Other objects and aspects as well as the several advantages of the invention will be apparent to those skilled in the art upon reading the specification and the appended claims.

In accordance with the invention, a process is provided for the production of acids and esters by reacting olefins with carbon monoxide and water or alcohols in the presence of trifluoromethanesulfonic acid.

In accordance with one embodiment of the invention, acids containing "2n+1" carbon atoms are produced by the reaction of at least one olefin containing n carbon atoms with carbon monoxide and water in the presence of trifluoromethanesulfonic acid.

In accordance with another embodiment of the invention, esters containing [(2n+1) + n'] carbon atoms are produced by reacting at least one olefin containing n carbon atoms with carbon monoxide and at least one alcohol having n' carbon atoms in the presence of trifluoromethanesulfonic acid.

In accordance with a further embodiment of the invention, esters containing [2(2n+1) + n'] carbon atoms are produced by the reaction of at least one olefin containing n carbon atoms with carbon monoxide and at least one diol having n carbon atoms in the presence of trifluoromethanesulfonic acid.

Olefins suitable for use in the present invention are described by the formula

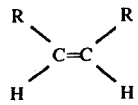

wherein R can be hydrogen or alkyl with the proviso that the two R radicals together can represent a tetramethylene grouping and the total number of carbon atoms in the olefin is between four and twelve. Examples of linear olefins which can be used in the present process are the following: 1-butene, cis-2-butene, trans-2-butene, 1-pentene, 2-pentene, 1-hexene, 2-hexene, 1-octene, 1-dodecene, 1-hexadecene, 3-heptene, 4-decene, and the like. The cyclic olefin found effective is cyclohexene. Olefins containing the grouping

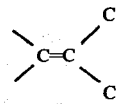

such as 2-methylpentene-2 and 2-methylbutene-2 did not give detectable amounts of ester in the present process. It is also to be noted from the examples that norbornene did not give a detectable amount of ester in the inventive process.

Alcohols suitable for use in the present invention are described by the formula

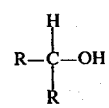

wherein R can be hydrogen, alkyl or hydroxyalkyl with the proviso that the two R groups together can represent an alkylene grouping selected from the group consisting of tetramethylene and pentamethylene and the total number of carbon atoms does not exceed 12.

Water can be used in the present invention rather than an alcohol for the production of acids rather than esters.

Alcohols suitable for use in the present invention contain one to twelve carbon atoms and presently preferred are primary alcohols such as methanol, ethanol, n-propanol, n-butanol, n-hexanol, n-octanol, n-dodecanol, and the like. Diols such as 1,4-butanediol, ethylene glycol, and the like are also suitable. Suitable secondary alcohols which can be used include 2-propanol and cyclohexanol. Alcohols such as allyl alcohol and benzyl alcohol are not suitable for use in the present process.

The present process can be carried out in a continuous, semi-continuous or batch manner with or without reaction diluents. The acid and ester products produced according to the invention can be recovered from the reaction mixture by well-known procedures including fractionation, crystallization, filtration, solvent extraction, and the like.

The reaction generally will be carried out at a temperature in the range of −50° to 100°C, preferably −20° to 50°C, with the reaction time generally varying from 5 minutes to 72 hours, more often varying from 30 minutes to 6 hours. The carbon monoxide pressure employed during the reaction will generally range from 25 to 5,000 psig, preferably 100 to 3,000 psig.

The mol ratio of olefin to trifluoromethanesulfonic acid will usually range from 0.1 to 3, preferably 0.3 to 1.5, and the mol ratio of olefin to alcohol or water will range from 0.15 to 7, preferably 0.4 to 2.5.

The reaction can be carried out in the presence of a solvent such as, for example, liquid $SO_2$ and 1,1,2-trichloro-1,2,2-trifluoroethane. Other reaction diluents such as fluorotrichloromethane, difluorodichloromethane, carbon tetrachloride, and chlorosulfurylfluoride can also be used when desired.

The reactants can be brought together in any desirable order. However, it is preferable to add the olefin to a mixture of the alcohol, carbon monoxide, and acid or the olefin and the alcohol to the carbon monoxide and acid in the preparation of esters. An analogous procedure can be followed in preparing acids from olefin, trifluoromethanesulfonic acid, water, and carbon monoxide.

SPECIFIC EXAMPLES

The present process is practiced in accordance with the two general methods described below.

a. Method I

Trifluoromethanesulfonic acid ($CF_3SO_3H$) and alcohol are placed in an ice cooled Hastelloy B reactor, and the system is pressured to 1,000–1,200 psig with carbon monoxide. The olefin is then pumped into the pressured reactor by means of a Whitely laboratory pump and during olefin addition the reaction mixture is agitated at the maximum stirring rate (2,500 rpm) for a specified time at the desired temperature. At the end of the reaction period, the system is vented and the reactor contents are poured over ice. The mixture is made basic with sodium hydroxide and extracted with ether. The ether extracts are dried over anhydrous magnesium sulfate and concentrated to give the ester product. Further purification can be effected by recrystallization and/or fractional distillation. Acidification of the alkaline aqueous phase remaining after the ether extraction provides a means of isolating acidic components in the reaction product mixture.

b. Method II

Trifluoromethanesulfonic acid is introduced under a nitrogen atmosphere into a 300 ml Hastelloy B autoclave cooled in a salt-ice bath. The alcohol is then added to the acid in a dropwise fashion with stirring and the temperature is maintained at +10°C or lower during this mixing. Rapid addition of the alcohol to the acid results in an undesirable exothermic reaction. Cold olefin is then layered on top of the quiescent alcohol-acid mixture. The reactor is capped and pressured with carbon monoxide during which time the internal temperature is maintained at about −5° to 0°C. In order to maintain the temperature of the reaction mixture at +10°C or lower during the mixing of the reactants, the stirrer is operated initially at low speed and increased gradually in 200 rpm increments over a 10-30 minute period to reach a maximum stirring rate of 2,500 rpm. On reaching the maxmum stirring rate, the salt-ice bath is removed and the system allowed to warm to about 20°–40°C. The carbon monoxide pressure drop usually begins at about 15°C. At the end of a run the reactor is cooled to 0°C, vented, and the reaction mixture processed as described in Method I.

EXAMPLE I (Method I)

A 0.53 mol (17 g) sample of methanol and 0.34 mol (30 ml, 51 g) trifluoromethanesulfonic acid were placed in a Hastelloy B reactor and pressured to 1,200 psig with carbon monoxide. Cyclohexene (0.5 mol, 41 g) was pumped into the reactor over a 1-hour period and then the reaction mixture was stirred for three hours at 25°–27°C. The reactor was cooled, vented and the reaction mixture was poured on ice. Ammonium hydroxide was added to render the mixture basic before extracting with ether. The ether extract was dried and concentrated to give 51.8 g pale yellow oil. Some spillage occurred on filtering this oil to remove a small quantity of solid matter and a subsequent concentration of a pentane solution of the oil gave 36.5 g of residue. A 34.2 g portion of this residue was distilled through a six-inch vacuum jacketed Vigreux column to give a 27.76 g fraction of colorless liquid which boild at 100°–105°c/0.2–0.7 mm and possessed a refractive index of 1.4861. Infrared analysis indicated the presence of an ester grouping and nuclear magnetic resonance indicated the presence of a methoxy grouping ($OCH_3$) and the presence of two cyclohexyl groups per methoxy group. A 26.15 g portion of the above colorless oil was redistilled to give a 15.73 g fraction which boiled at 85°–87°C/0.4 mm and exhibited a refractive index of 1.4863. Elemental analysis on this fraction gave the following results:

Calculated for $C_{14}H_{24}O_2$: C, 74,95; H, 10.78. Found: C, 75.27; H, 10.42.

Based on the foregoing data, the product was tentatively identified as the methyl ester of 1-bicyclohexylcarboxylic acid [lit. b.p. 150°–1°C/17 mm, Chemical Abstracts, 55, 10349 (1961)].

To further characterize the product from the above run (presumably an ester) a reduction was effected with a commercially available reductant, $NaAlH_2(OCH_2CH_2OCH_3)_2$ in benzene. The infrared analysis of the product from this reduction indicated the presence of hydroxyl and the absence of carbonyl which would be consistent with the reduction of an ester to an alcohol. A sample of the "reduced ester" was purified by sublimation at 40°–50°C/0.3 mm. A phenylurethane was prepared by treating a portion of the sublimed material with phenylisocyanate. The phenylurethane derivative was recrystallized from hexane to give white needles melting at 119°–120°C. This melting point is in good agreement with the 118°C melting point reported for the phenylurethane derivative of 1-bicyclohexylmethanol (Bull. Soc. Chim. France, 1954, 497). The above data indicate that the ester product of the inventive process is methyl 1-bicyclohexylcarboxylate. Product from a similar run was shown to have a molecular weight of 224 by mass spectral analysis (calculated molecular weight for methyl 1-bicyclohexylcarboxylate, $C_{14}H_{24}O_2$, is 224).

EXAMPLE II (Method II)

A 300 ml Hastelloy autoclave was cooled in ice under a nitrogen atmosphere and 0.68 mol (102 g, 60 ml) trifluoromethanesulfonic acid was added. A 0.53 mol (17 g) sample of methanol was added dropwise to the reactor with stirring since the addition is accompanied by the evolution of heat. A 0.5 mol (41 g) sample of cyclohexene was layered on top of the quiescent trifluoromethanesulfonic acid/methanol mixture and the reactor was capped and pressured to 1,140 psig with carbon monoxide. Stirring of the reaction mixture was carried out at a controlled rate initially so that the temperature never exceeded 0°C in the first 20 minutes of the reaction period. During this 20-minute period stirring was gradually increased to a maximum speed of 2,500 rpm. After 20 minutes, the ice bath was removed and the temperature of the reaction mixture was allowed to increase to 30°–32°C. Carbon monoxide pressure was maintained in the range of 1,110–1,150 psig during a total reaction time of 3 hours. At the end of the reaction period, the reactor was cooled in a salt-ice bath, vented, and the light brown reaction mixture was poured into ice water. This mixture was made basic with 20% sodium hydroxide solution and extracted with three 200 ml portions of ethyl ether. The combined ether extracts were dried over anhydrous magnesium sulfate and concentrated to 52.1 g of yellow oil. Gas chromatographic analysis of this oil indicated the following composition:

| Component # | Area % |
| --- | --- |
| Methyl 1-bicyclohexylcarboxylate | 82.6 |
| Cyclohexene (A) | 0.2 |
| Cyclohexyl methyl ether (B) | 7.0 |
| Methyl 1-methylcyclopentylcarboxylate (C) | 1.1 |
| Methyl cyclohexylcarboxylate (D) | 7.8 |
| 1-Cyclohexylcyclohexene (E) | 0.5 |
| Unknown | 0.8 |

Components (A)–(E) exhibited glc retention times comparable to glc retention times of authentic samples. The glc retention time of methyl 1-bicyclohexylcarboxylate was comparable to the glc retention time of the dimer ester produced in Example I. Components (C) and (D) are the conventional Koch type reaction products. Component (B) is the expected ether product from the known acid promoted etherification of cyclohexene with methanol. Component (E) is the expected acid promoted dimerization product of cyclohexene.

A 49.65 g sample of the yellow oil was distilled to give 37.71 g of methyl 1-bicyclohexylcarboxylate ($n_D^{20}$ 1.4864; b.p. 97°–98°C/1.0 mm).

EXAMPLE III (Liquid SO$_2$ Diluent)

A 100 ml sample of liquid sulfur dixoide was prepared by passing SO$_2$ gas into a 300 ml 3-necked round bottomed flask chilled in a −80°C bath. A 0.34 mol (51.0 g, 30 ml) samle of trifluoromethanesulfonic acid was then added to the cold liquid SO$_2$ followed by the dropwise addition of 0.34 mol (10.8 g) methanol at about −45°C. A 0.34 mol (27.8 g) sample of cyclohexene was then added at −55°C over a five minute period. At this point the mixture was yellow and not homogeneous. However, on warming to −45°C the mixture became homogeneous. The reaction mixture was transferred to a Hastelloy B reactor and pressured to about 1,200 psig with carbon monoxide. The maximum pressure observed during the run was 1,480 psig. During a reaction period of approximately 4.5 hours, stirring was carried out at 2,500 rpm, and the reaction temperature gradually increased from −74°C to about +15°C.

At the end of the reaction period, the homogeneous reaction mixture was cooled to −35°C, vented and mixed with ice water. This mixture was extracted with ether and the ethereal extract was washed successively with water, aqueous sodium hydroxide, and finally again with water. The ether solution was dried and concentrated to 32.3 g of residual oil. A 29.15 g portion of the above oil was distilled to give a 19.76 g faction of methyl 1-bicyclohexylcarboxylate (the "dimer ester" from cyclohexene).

EXAMPLE IV (Method I with 1,1,2-trichloro-1,2,2-trifluoroethane diluent)

The following reactants were placed in a cold 300 ml Hastelloy reactor: 0.34 mol (51.0 g, 30 ml) trifluoromethanesulfonic acid, 60 ml 1,1,2-trichloro-1,2,2-trifluoroethane, and 0.26 mol (8.5 g) methanol. The reactor was capped and pressured to 1,220 psig with CO. Cyclohexene (20.5 g, 0.25 mol) was pumped into the reactor at 22°–29°C over a 22 minute period and then the reaction mixture was stirred for three hours at 30°–32°C. The reactor was cooled, vented, and the reaction mixture poured over ice, neutralized with base and extracted with ether. The ether extract was dried and concentrated to 25.1 g of residue. A glc analysis of this product showed the following components identified by glc retention times of authentic samples:

| Components | Area % |
| --- | --- |
| Cyclohexene | 1.4 |
| Methyl Cyclohexyl Ether | 13.7 |
| 1-Methyl-1-cyclopentanecarboxylate | 1.1 |
| Methyl Cyclohexanecarboxylate | 10.9 |
| 1-Cyclohexylcyclohexene | Trace |
| Methyl 1-Bicyclohexylcarboxylate | 72.2 |
| Unknown | 0.7 |

EXAMPLE V (Method II)

A 0.68 mol (102 g, 60 ml) samle of trifluoromethanesulfonic acid under a nitrogen atmosphere was placed in a 300 ml Hastelloy autoclave cooled in an ice bath. Cyclohexanol (50 g, 0.50 mol) was added to the reactor followed by cyclohexene (41.0 g, 0.50 mol) which was layered on top of the quiescent alcohol-acid mixture. The reactor was capped and pressured to 1,200 psig with CO. The stirring rate was gradually increased during the run as described in the general procedure for Method II. During the four-hour reaction period, the temperature varied from −5°C to +32°C and pressure varied from 1,200 psig initially down to a final reading of 695 psig. At the end of the reaction period, the system was cooled to 0°C, vented, and the reaction mixture poured on ice, neutralized with base and extracted with ether. The ether extract was concentrated to 68.5 g of a dark viscous residue. A 64.73 g sample of the residue was distilled to give a 31.83 fraction (130°–145°C/0.4 mm) which exhibited a single major peak (87.2 area %) by glc analysis. An additional distillation of a 26.62 g portion of the above product gave 22.12 g product (141°–145°C/0.4 mm) with a refractive index of 1.4975.

Elemental and molecular weight analysis: Calculated for $C_{19}H_{32}O_2$: %C, 7803; %H, 10.95; Mol. wt., 292. Found: %C, 77.96, %H. 11.06 Mol. wt. (mass spectral analysis), 282.

Nuclear magnetic resonance analysis in conjunction with the above data confirmed the major product to be cyclohexyl 1-bicyclohexylcarboxylate ($C_{19}H_{32}O_2$).

EXAMPLE VI (Method II with 1,1,2-trichloro-1,2,2-trifluoroethane diluent)

A 0.34 mol (51.0g, 30 ml) sample of trifluoromethanesulfonic acid was dissolved in 60 ml 1,1,2-trichloro-1,2,2-trifluoroethane contained in a 300 ml Hastelloy reactor. A 0.26 mol (26.6 g) sample of 1-hexanol was added to the reactor followed by 0.25 mol (20.5 g) cyclohexene which was layered on top of the quiescent reactor mixture. The reactor was capped and pressured to 1,200 psig CO. The rate of stirring was gradually increased from an initial rate of 200 rpm to 2,500 rpm during the first 15 minutes of the reaction period. During a reaction period of about 5.33 hours, the pressure slowly decreased from 1,200 psig to 800 psig and temperature varied from −3.5°C to +32°C. Workup was essentially the same as described in Example V and concentration of the ethereal extract gave 43.5 g residue. A 40.82 g portion of this crude product mixture was distilled to give a 16.28 g fraction which was collected at 128°C/0.4 mm. A 15.36 g portion was redistilled to give 12.02 g product (122°–126°C/0.4 mm) which possessed a refractive index of 1.4772.

Elemental and molecular weight analysis: Calculated for $C_{19}H_{34}O_2$: %C, 77.49; %H, 11.64; Mol. Wt., 294. Found: %C, 77.62; %H, 11.72; Mol wt., 283.

The above data in conjunction with nuclear magnetic resonance analysis confirmed the product to be n-hexyl 1-bicyclohexylcarboxylate ($C_{19}H_{34}O_2$).

EXAMPLE VII (Method II)

A 300 ml Hastelloy autoclave was cooled in ice under a nitrogen atmosphere and 0.68 mol (60 ml, 102 g) trifluoromethanesulfonic acid was added. A 0.27 mol (35 g) sample of 1-octanol was added to the reactor followed by 0.5 mol (41 g) cyclohexene which was carefully layered on top of the quiescent reaction mixture. The reactor was capped and pressured to 1,180 psig CO. The rate of stirring was gradually increased from an initial rate of 200 rpm to a maximum of 2,500 rpm during the first 22 minutes of the run. During a reaction period of 187 minutes, temperature varied from −2.5°C to +32°C and pressure gradually decreased from a maximum of 1,180 psig to a final reading of 680 psig. Workup was essentially the same as described in Example IV giving 73.35 g residue after concentration of the ether extract. Distillation of a 71.05 g portion of this crude product mixture gave a 24.53 g fraction boiling at 145°–152°C/0.2 mm with a refractive index of 1.4790. Redistillation of a 23.25g sample of the above fraction gave 21.19 g product boiling at 144°–145°C/0.2 mm with a refractive index of 1,4782.

Elemental and molecular weight analysis: Calculated for $C_{21}H_{38}O_2$: %C, 78.20; %H, 11.88; Mol. wt. 322.5. Found: %C, 78.68; %H, 11.84; Mol. wt. 311 (mass spectral analysis).

The above data in conjunction with nuclear magnetic resonance analysis confirmed the product to be n-octyl-1-bicyclohexylcarboxylate ($C_{21}H_{38}O_2$).

The expected Koch type reaction product, n-octyl cyclohexane carboxylate, was identified as the major component in a fraction which weighed 18.39 g (89°–110°C/0.2 mm). Redistillation of this fraction gave n-octyl cyclohexanecarboxylate.

Elemental and molecular weight analysis: Calculated for $C_{15}H_{28}O_2$: %C, 74.94; %H, 11.73; Mol. wt. 240.4; Found: %C, 75.70; %H, 11.73; Mol. wt. (vapor density method) 240.

Nuclear magnetic analysis data were consistent with the proposed structure.

EXAMPLE VIII (Method II)

This run involved the use of the following reactants: 0.68 mol (102 g, 60 ml) trifluoromethanesulfonic acid, 0.25 mol (22.5 g) 1,4-butanediol, and 0.5 mol (41 g) cyclohexene. The system was pressured to 1,200 psig with CO. The apparatus and procedure were essentially the same as described in Example V. During the three hour reaction period, the temperature varied from −2.5°C to +41°C and pressure varied from an initial value of 1,200 psig to 790 psig. The ether extract was concentrated to give 54.4 g of residue. A 52.3 g portion of this residue was distilled to give a 4.90 g fraction (131°–134°C/0.2 mm) and a 33.62 g fraction of a very viscous liquid (134°–255°C/0.5 mm). A 31.25 g portion of this viscous liquid was redistilled to give 4.37 g of material (245°–250°C/0.3 mm) which crystallized in the receiver. Recrystallization from n-pentane gave white crystals which softened at 81°C and melted at 84.5°–87°C. Infrared analysis indicated the presence of a carbonyl group but no carboxyl group.

Elemental and molecular weight analysis: Calculated for $C_{30}H_{50}O_4$: %C, 75.9; %H, 10.62; Mol. wt. 474.7. Found: %C, 75.92; %H, 10.35; Mol. wt. 454 (mass spectral analysis).

The above data in conjunction with nuclear magnetic resonance analysis confirmed the product to be the diester of 1,4-butanediol and 1-bicyclohexylcarboxylic acid ($C_{30}H_{50}O_4$).

To further characterize the 4.90 g fraction (131°–134°C/0.2 mm) isolated above, the material was recrystallized from n-pentane to give white crystals which melted at 121°–123°C.

Elemental analysis: Calculated for $C_{13}H_{22}O_4$: %C, 74.24; %H, 10.54. Found: %C, 74.06; %H, 10.58.

Mass spectral and nuclear magnetic resonance analyses in conjunction with the elemental analysis indicated the product to be 1-bicyclohexylcarboxylic acid ($C_{13}H_{22}O_2$) [lit.m.p. 121°–123°C; J. Amer. Chem. Soc., 68, 828 (1946)].

The following example demonstrates that the use of water in the inventive process rather than alcohol gives rise to "dimer acid" rather than "dimer ester."

EXAMPLE IX (Method II)

This run involved the use of the following reactants: 0.68 mol (102 g, 60 ml) trifluoromethanesulfonic acid, 0.5 mol (9 g) water and 0.5 mol (41 g) cyclohexene. The system was pressured to 1,180 psig with carbon monoxide. The apparatus and run procedure were essentially the same as described in Example V except that water rather than aqueous base was used in the workup. Temperature varied from +2.5°C to +34°C and pressure varied from 1,180 psig to 780 psig during the three-hour run. The ether extract was concentrated to give 49.78 g of residue which on distillation gave an 18.02 g fraction (75°–87°C/1.2 mm) identified as a mixture of cyclohexanecarboxylic acid and 1-methyl-1-cyclopentanecarboxylic acid. Three additional fractions weighing 3.32 g, 4.82 g, and 8.51 g collected over the range 140°–153°C/1.2 mm were combined, recrystallized from n-hexane, and identified as 1-bicyclohexylcarboxylic acid, white crystals, m.p. 121°–123°C [lit. m.p. 121°–123°C; J. Amer. Chem. Soc., 68, 828 (1946)].

EXAMPLE X (Method II)

This run involved the use of the following charge: 0.68 mol (102 g, 60 ml) trifluoromethanesulfonic acid, 0.50 mol (23 g) ethanol and 0.50 mol (41 g) cyclohexene. The system was pressured to 1,200 psig with CO and the run was carried out in accordance with the general procedure of Method II. Temperature varied from −3.5°C to +32°C during the reaction period of three hours. The ether extract was concentrated to give a 57 g residue. A 54.65 g portion of this residue was distilled to give a 42.60 g fraction (105°C/0.3 mm) with a refractive index of 1.4809. This fraction exhibited a single major glc peak (98.6 area %) at a retention time of about 14.5 minutes which is close to that exhibited by methyl 1-bicyclohexylcarboxylate (about 13.5 minutes). On the basis of the above it was concluded that the 42.60 g fraction was ethyl 1-bicyclohexylcarboxylate (lit. b.p. 130.5°C/4 mm; b.p. 139°–145°C/6–8 mm; U.S. Pat. No. 2,659,750).

EXAMPLE XI

Method II with 1,1,2-trichloro-1,2,2-trifluoroethane

A mixture of 0.34 mol (51 g, 30 ml) trifluoromethanesulfonic acid and 30 ml 1,1,2-trichloro-1,2,2-trifluoroethane was placed in a cold 300 ml Hastelloy reactor. A 0.25 mol (18.5 g) sample of n-butanol was added to the reactor followed by 30 ml 1,1,2-trichloro-1,2,2-trifluoroethane and a layer of cyclohexene (20.5 g, 0.25 mol). The reactor was capped and pressured to 1,190 psig with carbon monoxide. The stirring rate was gradually increased from 200 rpm to a maximum of 2,500 rpm over a period of 15 minutes. During the 203 minute reaction period, the temperature varied from −4.5°C to +31°C and the pressure varied from 1,190 psig to 915 psig. Workup was essentially the same as described in Example V and concentration of the ether extract gave 25.37 g of residue. Distillation of a 22.23 g portion of this residue gave 14.31 g of a fraction (105° –110°C/0.3 mm) which exhibited a refractive index of 1.4792.

Elemental and molecular weight analysis: Calculated for $C_{17}H_{30}O_2$: %C, 76.64; %H, 11.35; Mol. Wt. 266.4. Found: %C, 76.58; %H, 11.31; Mol. wt. 261 (mass spectral analysis).

Nuclear magnetic resonance analysis together with the above data indicate the product to be the n-butyl ester of 1-bicyclohexylcarboxylic acid ($C_{17}H_{30}O_2$). (lit. b.p. 93°–95°C/0.06 mm, U.S. Pat. No. 2,659,750).

EXAMPLE XII (Method II with 1,1,2-trichloro-1,2,2-trifluoroethane diluent)

A 0.34 mol (50.5 g, 30 ml) sample of trifluoromethanesulfonic acid was placed in a 300 ml Hastelloy reactor cooled in an ice bath. A 0.25 mol (15 g) portion of isopropanol was slowly added to the acid followed by a layer of 0.25 mol (20.5 g) cyclohexene dissolved in 60 ml of 1,1,2-trichloro-1,2,2-trifluoroethane. The reactor was capped and pressured to 1,210 psig with carbon monoxide. The reaction was carried out and worked up in the same manner as described in Example X. Concentration of the ether extract gave a 21.08 g residue. A glc analysis of the crude sample showed a major component as evidenced by a 61.6 area % peak. Distillation of a 19.22 g portion of the residue met with a great deal of difficulty due to foaming. A 6.92 g fraction (92°–94°C/1 mm) was finally isolated and characterized by the following analysis:

Calculated for $C_{16}H_{28}O_2$: %C, 76.13; %H, 11.2. Found: %C, 76.1; %H, 11.1.

A 2.40 g sample of the above fraction was redistilled to give 0.68 g (92°–98°C/0.8 mm) of material which was shown to be isopropyl 1-bicyclohexylcarboxylate ($C_{16}H_{28}O_2$) by infrared, nuclear magnetic resonance and elemental analyses. The molecular weight was determined to be 250 as compared to 252 for $C_{16}H_{28}O_2$.

EXAMPLE XIII (Method II)

A 0.5 mol (31 g) sample of 1,2-ethanediol was added to a mixture of 0.68 mol (102 g, 60 ml) trifluoromethanesulfonic acid and 0.5 mol (41 g) cyclohexene in a Hastelloy B reactor at 0°C. The reactor was capped and pressured to 1,210 psig with CO. This run was carried out essentially in the same manner as described in Example II except that the reaction was started at 29.5°C and at the end of a 3.5 hour reaction period the temperature had increased to 42.5°C. During the run, the pressure decreased from 1,210 psig to 995 psig. Reaction workup gave an ether extract which was concentrated to 55.6 g of residue. This residue was distilled up to 104°C/0.9 mm at which point the distillation was stopped. The kettle material weighed 28.30 g and was transferred to another apparatus fitted with a short path distillation column. A 22.21 g portion of the above kettle material gave a 12.43 g fraction (240°–265°C/0.7 mm) of a very viscous liquid with a refractive index of 1.4644. A final distillation of a 12.03 g sample of the above viscous liquid gave 9.41 g of sample for characterization.

Elemental and molecular weight analysis: Calculated for $C_{30}H_{50}O_5$: %C, 73.5; %H, 10.2; Mol. wt. 490. Found: %C, 73.49; %H, 10.22; Mol wt. 476.

Nuclear magnetic resonance and mass spectral analyses in conjunction with the above data indicated that the product was the diester of diethylene glycol and 1-bicyclohexylcarboxylic acid ($C_{30}H_{50}O_5$). The characterization data did not indicate the presence of an appreciable amount of the diester of ethylene glycol and 1-bicyclohexylcarboxylic acid.

TABLE I

Table I summarizes a number of runs described in Examples I–XIII which are representative of the inventive process using cyclohexene as the feed olefin with a variety of alcohols.
1-Bicyclohexylcarboxylates ("Dimer Esters") from the Reaction of Cyclohexene with Various Alcohols in the Presence of CO and $CF_3SO_3H^x$

| Example No. | Alcohol | Dimer Esters Formula | Solvent | Method of Preparation | Name of Dimer Ester[a] | Comments |
|---|---|---|---|---|---|---|
| I | Methanol | $C_{14}H_{24}O_2$ | — | I | Methyl 1-bicyclohexyl-carboxylate | Dimer ester refractive index 1.4863 |
| II | Methanol | $C_{14}H_{24}O_2$ | — | II | Methyl 1-bicyclohexyl-carboxylate | Minor Products[b] |
| III | Methanol | $C_{14}H_{24}O_2$ | $SO_2$ | # | Methyl 1-bicyclohexyl-carboxylate | Minor Products[b] |
| IV | Methanol | $C_{14}H_{24}O_2$ | F–C(Cl)–C(Cl)–Cl (F,F) | I≠ | Methyl 1-bicyclohexyl-carboxylate | Minor Products[b] |
| V | Cyclohexanol | $C_{19}H_{32}O_2$ | — | II | Cyclohexyl 1-bicyclohexylcarboxylate | Dimer Ester refractive index 1.4975 |

3,965,132

TABLE I-continued

Table I summarizes a number of runs described in Examples I–XIII which are representative of the inventive process using cyclohexene as the feed olefin with a variety of alcohols.
1-Bicyclohexylcarboxylates ("Dimer Esters") from the Reaction of Cyclohexene with Various Alcohols in the Presence of CO and $CF_3SO_3H^x$

| Example No. | Alcohol | Dimer Esters Formula | Solvent | Method of Preparation | Name of Dimer Ester[h] | Comments |
|---|---|---|---|---|---|---|
| VI | 1-Hexanol | $C_{19}H_{34}O_2$ |  | II[≠] | n-Hexyl 1-bicyclohexylcarboxylate | Dimer Ester refractive index 1.4772 |
| VII | 1-Octanol | $C_{21}H_{38}O_2$ | — | II | n-Octyl 1-bicyclohexylcarboxylate | Approximately the same weight of n-octyl cyclohexanecarboxylate was produced |
| VIII | 1,4-Butanediol | $C_{30}H_{50}O_4$ | — | II | 1,4-Butanediol bis(1-bicyclohexylcarboxylate) | |
| XI | 1-Butanol | $C_{17}H_{30}O_2$ |  | II[≠] | n-Butyl 1-bicyclohexylcarboxylate | Minor Products[c] |
| XII | 2-Propanol | $C_{16}H_{28}O_2$ | " | II[≠] | Isopropyl 1-bicyclohexylcarboxylate | Minor Products[d] |
| XIII | 1,2-Ethanediol | $C_{30}H_{50}O_5$ | — | II | 2,2'-Oxydiethyl bis(1-bicyclohexylcarboxylate)[a] | Minor Products[e] |
| IX | Water[r] | $C_{13}H_{22}O_2$ | — | II | "Dimer Acid" 1-bicyclohexylcarboxylic acid | Minor Products[f] |
| X | Ethanol | $C_{15}H_{26}O_2$ | — | II | Ethyl 1-bicyclohexylcarboxylate | Dimer ester refractive index 1.4809. Minor Products[g] |

[r]Water was used in place of alcohol to give the "dimer acid" 1-bicyclohexylcarboxylic acid ($C_{13}H_{22}O_2$) in Example IX.
Liquid $SO_2$ diluent was used. Mixture was stirred at maximum rate of 2,500 rpm throughout the reaction period.
≠ 1,1,2-Trichloro-1,2,2-trifluoroethane diluent was used.
[a]Also called diethylene glycol bis(1-bicyclohexylcarboxylate).
[b]Cyclohexyl methyl ether, methyl cyclohexanecarboxylate, 1-methyl-1-cyclopentylcarboxylate, and 1-cyclohexyl cyclohexene.
[c]Cyclohexyl butyl ether, 1-methyl-1-butylcyclopentanecarboxylate, and butyl cyclohexanecarboxylate.
[d]1-Bicyclohexylcarboxylic acid.
[e]1-Hydroxyethyl cyclohexyl ether.
[f]Cyclohexanecarboxylic acid and 1-methyl-1-cyclopentanecarboxylic acid.
[g]Cyclohexylethyl ether and ethyl cyclohexanecarboxylate.
[h]As indicated hereinbefore, the terms "dimer acid" and "dimer ester" are used for convenience to define monobasic acids and the corresponding esters prepared with monohydroxylic alcohols or diols.

EXAMPLE XIV

(Method II)

A mixture of 0.68 mol (102 g, 60 ml) trifluoromethanesulfonic acid and 0.53 mol (17g) methanol was placed in a 300 ml Hastelloy reactor and chilled to −80°C. A 0.5 mol (28 g) sample of 1-butene was pressured into the reactor which was maintained in a dry ice bath during the butene-1 addition. The dry ice bath was replaced with an ice bath and the system was pressured to 1,200 psig with CO. Stirring was initiated at 200 rpm and gradually increased to a maximum of 2,500 rpm over a 19 minute period. At this point the temperature was about 0°C. The ice bath was removed and stirring was continued for a total reaction period of 105 minutes. The final temperature and pressure, respectively, were 30°C and 915 psig. Reaction workup was essentially the same as described in Example I and concentration of the ether extract gave a residue of 33.1 g. A 30.76 g portion of this residue was distilled to give a 10.44 g fraction (73°–74°C/13–14 mm) of dimer esters.

Elemental and molecular weight analyses: Calculated for $C_{10}H_{20}O_2$: %C, 69.73; %H, 11.70; Mol. wt. 172. Found: %C, 69.72; %H, 11.95; Mol. wt. 173.

The above data in conjunction with nuclear magnetic resonance and mass spectral analyses indicated that the product was a mixture of the erythro and threo diastereoisomers of methyl 2,3-dimethyl-2-ethylpentanoate ($C_{10}H_{20}O_2$).

EXAMPLE XV

(Method II)

A 0.53 mol (17 g) sample of methanol was added dropwise to 0.68 mol (102 g, 60 ml) trifluoromethanesulfonic acid in a Hastelloy B reactor cooled in an ice-salt bath. The reactor was capped and purged with nitrogen and then pressured with cis-2-butene (29 g, 0.52 mol) at a temperature of −68°C. After warming the system up to about 0°C, the reactor was pressured to 1,200 psig with CO. The stirring rate was gradually increased to a maximum of 2,500 rpm over a period of 14 minutes. During the three-hour reaction period, temperature varied from −5°C to +31.5°C and pressure varied from 1,200 psig to 815 psig. The reaction mixture was worked up as described in Example V and the ether extract concentrated to 38.8 g residue. This residue was distilled at ~78°C/14 mm to give 30.08 g of distillate. A 29.54 g portion of this distillate was redistilled to give a 22.61 g fraction (64°C/7.5–8 mm) which had a refractive index of 1.4299. According to glc, 1H nuclear magnetic resonance, and $^{13}C$ nuclear magnetic resonance analyses indicated that the two major components (~84 area %) of the 22.61 g fraction were the erythro and threo diastereoisomers of methyl 2,3-dimethyl-2-ethylpentanoate ($C_{10}H_{20}O_2$). The erythro and threo diastereoisomeric mixture of methyl 2,3-dimethyl-2-ethylpentanoate was independently synthesized by the reaction of 3,4-dimethyl-3-hexanol with CO and methanol in liquid HF. The product exhibited the same glc retention time and infrared spectrum as the product from the reaction of butene with CO, $CH_3OH$ and trifluoromethanesulfonic acid.

EXAMPLE XVI (Method II)

This run involved the use of trans-2-butene and was carried out in essentially the same fashion as described for cis-2-butene in Example XV. Work-up yielded 33 g of residue from the ether extract. A 32.19 g portion of this residue gave several fractions one of which weighed 5.10 g (80°–98°C/1–4 mm) and contained methyl 2,3-dimethyl-2-ethylpentanoate as the major component as verified by glc and mass spectral analyses.

EXAMPLE XVII (Method II)

To a cold quiescent mixture of 0.53 mol (17 g) methanol and 0.68 mol (102 g, 60 ml) trifluoromethanesulfonic acid in a Hastelloy B reactor was added a layer of 0.5 mol (35 g) 1-pentene. The reactor was capped and pressured to 1,190 psig with carbon monoxide. This reaction was carried out and worked up in essentially the same manner as described in other "Method II" runs. Concentration of the ether extract gave a 43.1 g residue. Distillation of this residue gave two fractions which weighed 24.69 g (63°C/1.8 mm) and 4.18 g (61°–85°C/1.2–2.0 mm). These fractions were combined, washed with sodium carbonate until neutral and then extracted with ether. The ether extract was dried and concentrated to give a residue which was redistilled. The second distillation gave a 23.36 g fraction (63°–63.5°C/2.1 mm) for analysis which had a refractive index of 1.4378.

Elemental and molecular weight analyses: Calculated for $C_{12}H_{24}O_2$: %C, 71.95; %H, 12.08; mol. wt., 200. Found: %C, 71.87; %H, 12.26; mol. wt., 202.

The above data in conjunction with the results of mass spectral and nuclear magnetic resonance analyses indicated one carbomethoxy group for each two $C_5$ moieties which is consistent with a $C_{12}H_{24}O_2$ isomeric mixture of esters. The isomers ($C_{12}H_{24}O_2$) appeared to constitute about 90% of the fraction which was characterized.

EXAMPLE XVIII (Method II)

This run was carried out in essentially the same manner as Example XVII except for the substitution of 2-pentene for 1-pentene in the charge. Concentration of the ether extract gave a 39.8 g residue. A 38.55 g portion of this residue was distilled to give a 27.36 g fraction (84°C/6–6.5 mm) which had a refractive index of 1.4368. A 26.59 g portion of the above material was redistilled to give a 23.18 g fraction (77°–78°C/4–5 mm) with a refractive index of 1.4368.

Elemental and molecular weight analyses: Calculated for $C_{12}H_{24}O_2$: %C, 72.0; %H, 12.0; Mol. wt. 200. Found: %C, 72.17; %H, 11.95; mol. wt. 221.

Mass spectral and nuclear magnetic resonance analyses in conjunction with the above results indicated one carbomethoxy group for each two $C_5$ units which is consistent with a $C_{12}H_{24}O_2$ isomeric mixture of "dimer esters."

EXAMPLE XIX (Method II)

This run was carried out in essentially the same manner as the pentene runs except for the use of 0.5 mol (42 g) 1-hexene in place of pentene. Concentration of the ether extract gave a 48.1 g residue. Distillation of this residue gave a 20.86 g fraction (76°–80°C/1 mm) and a 12.92 g fraction (80°–90°C/1–3 mm). These fractions were combined and redistilled to give 20.95 g of product (68°–84°C/1 mm) with a refractive index of 1.4411.

Elemental and molecular weight analyses: Calculated for $C_{14}H_{28}O_2$: %C, 73.6; %H, 12.3; Mol. wt. 228. Found: %C, 72.5; %H, 12.1; Mol. wt. 228 (vapor density).

The above results in conjunction with mass spectral and nuclear magnetic resonance data indicate the presence of one carbomethoxy group for each two $C_6$ units which is consistent with a $C_{14}H_{28}O_2$ mixture of "dimer ester" isomers. The "dimer ester" isomers ($C_{14}H_{28}O_2$) were the major components in the fraction which was characterized.

EXAMPLE XX (Method II)

This run used 0.5 mol (56 g) 1-octene in the charge and was carried out in essentially the same manner as the pentene runs of Examples XVII and XVIII and the 1-hexene run of Example XIX. Concentration of the ether extract gave a 65.4 g residue. A 64.13 g portion of this residue was distilled to give a 36.70 g fraction (90°–115°C/0.9–1 mm). A 35.58 g sample of this fraction was redistilled to give 27.83 g of product (100°–104°C/0.8 mm) with a refractive index of 1.4476.

Elemental and molecular weight analyses: calculated for $C_{18}H_{36}O_2$: %C, 75.97; %H, 12.77; mol. wt. 284. Found: %C, 76.60; %H, 12.99; mol. wt. 285.

The above results indicate that the product contains $C_{18}H_{36}O_2$ isomeric "dimer esters."

EXAMPLE XXI (Method II)

This run used 0.5 mol (84.2 g) 1-dodecene in the charge and was carried out in essentially the same manner as described in Examples XVI–XIX. Concentration of the ether extract gave a 92.88 g residue. A 90.33 g portion of this residue was distilled to give a 31.09 g fraction (82°–93°C/1.0–1.5 mm) and a 51.82 g kettle residue. A 48.59 g portion of the kettle residue was distilled to give a 2.05 g fraction (90°–165°C/0.8 mm), a 12.96 g fraction (165°–176°C/0.8 mm), and a 27.36 g fraction (176°–191°C/0.8 mm). These fractions were combined and a 41.48 g portion was redistilled to give a 38.21 g fraction (160°–183°C/0.8 mm) with a refractive index of 1.4550.

Elemental and molecular weight analyses: Calculated for $C_{26}H_{52}O_2$: %C, 78.72; %H, 13.22; mol. wt. 396.7. Found: %C, 78.8; %H, 13.2; mol wt. 366.

The above data in conjunction with mass spectral and nuclear magnetic resonance data indicated the presence of one carbomethoxy group for each two $C_{12}$ units which is consistent with a $C_{26}H_{52}O_2$ mixture of "dimer ester" isomers.

A 30.31 g portion of the above 31.09 g fraction was distilled to give a 16.49 g fraction (60°–71°C/0.8 mm) and an 11.73 g fraction (71°–78°C/0.8 mm). These fractions were combined and characterized by mass spectral, nuclear magnetic resonance, molecular weight and elemental analyses.

Elemental analysis: %C, 75.5; %H, 12.9; Mol. wt. 218.

The elemental analysis and molecular weight are in agreement with a mixture containing ⅔ by weight isomeric methyl tridecanoates (Koch type product) and ⅓ by weight isomeric methyl dodecyl ethers.

-continued

| Components | Area % |
| --- | --- |
| 1-Cyclohexylcyclohexene | Trace |
| 1-Bicyclohexylcarboxylic acid | 1.7 |
| Methyl 1-bicyclohexylcarboxylate | 34.4 |

A 26.82 g portion of the above residue was distilled to give an 11.9 g fraction (52°–62°C/2–9 mm) of 1-methyl-1-cyclopentanecarboxylate and methyl cyclohexanecarboxylate, and a 6.57 g fraction (104°–106°C/1 mm) of methyl 1-bicyclohexylcarboxy-

TABLE II

Table II summarizes a number of runs described in Examples XIV–XXI which are representative of the inventive process using methanol with a variety of olefins. "Dimer Esters" from the Reaction of Linear Olefins with Methanol in the Presence of CO and $CF_3SO_3H$

| Example No. | Olefin | Dimer Esters (Formula) | Method of Preparation | Name of Dimer Ester[f] (Mixture of Isomers) | Comments |
| --- | --- | --- | --- | --- | --- |
| XIV | 1-Butene | $C_{10}H_{20}O_2$ | II | Methyl 2,3-dimethyl-2-ethylpentanoate[a] | 31 unidentified components constituted 7% of the fraction characterized. |
| XV | cis-2-Butene | $C_{10}H_{20}O_2$ | II | Methyl 2,3-dimethyl-2-ethylpentanoate[a] | |
| XVI | trans-2-Butene | $C_{10}H_{20}O_2$ | II | Methyl 2,3-dimethyl-2-ethylpentanoate[a] | Complex mixture of 30 compounds. |
| XVII | 1-Pentene | $C_{12}H_{24}O_2$ | II | See footnote [b] | |
| XVIII | 2-Pentene | $C_{12}H_{24}O_2$ | II | See footnote [b] | |
| XIX | 1-Hexene | $C_{14}H_{28}O_2$ | II | See footnote [c] | Glc analysis of crude mixture showed ca. 92 area % dimer esters. |
| XX | 1-Octene | $C_{18}H_{36}O_2$ | II | See footnote [d] | |
| XXI | 1-Dodecene | $C_{26}H_{52}O_2$ | II | See footnote [e] | Methyl dodecyl ether and methyl tridecanoate were also produced. |

[a] Major components were the erythro and threo diastereoisomers which were independently synthesized from the reaction of 3,4-dimethyl-3-hexanol with CO and $CH_3OH$ in liquid HF.
[b] Characterization showed one carbomethoxy group for each two $C_5$ units.
[c] Characterization showed one carbomethoxy group for each two $C_6$ units.
[d] Characterization showed one carbomethoxy group for each two $C_8$ units.
[e] Characterization showed one carbomethoxy group for each two $C_{12}$ units.
[f] See footnote [h] for Table I.

The following examples (XXII–XXV) describe runs in which acids other than trifluoromethanesulfonic acid were used. Example III illustrating the process of the present invention with $CF_3SO_3H$ in liquid $SO_2$ was carried out in essentially the same manner as the runs described in Examples XXII–XXV. These runs show that the $CF_3SO_3H$ system produced predominantly the "dimer ester" methyl 1-bicyclohexylcarboxylate from cyclohexene whereas the other acid systems produced no ester products or produced predominantly the mono-ester methyl cyclohexanecarboxylate.

EXAMPLE XXII (Liquid $SO_2$ Diluent with Fluorosulfonic acid)

This run was carried out in the same manner as described in Example III with the following charge: 100 ml liquid $SO_2$, 0.34 mol (34.0 g, 19.5 ml) fluorosulfonic acid ($FSO_3H$), 0.34 mol (10.9 g) methanol, and 0.34 mol (27.9 g) cyclohexene. During a reaction period of 4 hours, stirring was carried out at 2,500 rpm and the reaction temperature gradually increased from −70°C to about +29°C. The usual workup and concentration of the ether extract gave 28.6 g of residue. Glc analysis of this residue showed the following composition:

| Components | Area % |
| --- | --- |
| Ether (from workup) | 3.0 |
| Cyclohexene | 5.2 |
| Cyclohexyl methyl ether | 1.2 |
| 1-Methyl-1-cyclopentanecarboxylate | 3.2 |
| Methyl cyclohexanecarboxylate | 51.3 | late.

EXAMPLE XXIII (Liquid $SO_2$ Diluent with Anhydrous HF)

This run was carried out in essentially the same manner as described in Example XXII with the following charge: 100 ml liquid $SO_2$, 0.34 mol (6.8 g, 7.0 ml) anhydrous HF, 0.34 mol (10.88 g) methanol, and 0.34 mol (27.88 g) cyclohexene. During a reaction period of 4 hours, stirring was carried out at 2,500 rpm and the reaction temperature gradually increased from −72°C to about +30°C. The ether extract was distilled at atmospheric pressure to leave a 15.96 g residue. Glc analysis of this residue indicated 99.8 area percent recovered cyclohexene and 0.2 area percent cyclohexyl methyl ether. No detectable amount of esters was observed in the reaction mixture.

EXAMPLE XXIV (Liquid $SO_2$ Diluent with $H_2SO_4$)

This run was carried out in essentially the same manner as Examples XXII and XXIII with the following charge: 100 ml liquid $SO_2$, 0.34 mol (33.32 g) $H_2SO_4$, 0.34 mol (10.88 g) methanol, and 0.34 mol (27.88 g) cyclohexene. During a reaction period of four hours, stirring was carried out at 2,500 rpm and the reaction temperature gradually increased from −65°C to +29°C. The ether extract was distilled at atmospheric pressure to leave a 20.24 g residue. Glc analysis of this residue indicated 84 area percent recovered cyclohexene, 12.5 area percent cyclohexanol, 1.6 area percent 1-cyclohexyl cyclohexene, and 1.9 area percent unidentified. There were no detectable amounts of esters.

EXAMPLE XXV (Liquid $SO_2$ Diluent with $CH_3SO_3H$)

This run was carried out in essentially the same manner as Examples XXII–XXIV with the following charge: 100 ml liquid $SO_2$, 0.34 mol (32.64 g) methanesulfonic acid, 0.34 mol (10.88 g) methanol, and 0.34 mol (27.88 g) cyclohexene. During a 4 hour reaction period, stirring was carried out at 2,500 rpm and the reaction temperature gradually increased from −66°C to +31°C. The ether extract was distilled at atmospheric pressure to leave a 20.5 g residue. Glc analysis of this residue showed 37.0 area percent ether (from extraction step), 60.5 area percent recovered cyclohexene, 1.7 area percent cyclohexanol or methyl cyclohexyl ether and 0.8 area percent 1-cyclohexyl cyclohexene.

The following summary (Table III) of Examples III, and XXII–XXV serves to distinguish the inventive process (Example III using $CF_3SO_3H$) over runs using other acid catalysts.

TABLE III

Summary of Examples III, XXII–XXV

| Example No. | Acid Catalyst | Major Detectable Products (distilled and/or glc area %) |
|---|---|---|
| III | $CF_3SO_3H$ | Methyl 1-bicyclohexylcarboxylate (19.76 g distilled). Undistilled sample showed 76.4 area percent methyl 1-bicyclohexylcarboxylate and 12.0 area percent methyl cyclohexane carboxylate. |
| XXII | $FSO_3H$ | Methyl 1-bicyclohexylcarboxylate (6.57 g distilled). Methyl cyclohexanecarboxylate and 1-methyl-1-cyclopentanecarboxylate (11.9 g distilled). |
| XXIII | HF | Unconverted cyclohexene (99.8 area percent). (No esters detected.) |
| XXIV | $H_2SO_4$ | Unconverted cyclohexene (84 area percent). Cyclohexanol (12.5 area percent). (No dimer ester detected.) |
| XXV | $CH_3SO_3H$ | Unconverted cyclohexene. (No esters detected.) |

Gas chromatographic analyses were carried out on a Hewlett-Packard Model 5752-B instrument with thermal conductivity detector cell and a 20-ft. × ⅛ in. 20% SE 30 on Chromasorb W, Reg. 60/80 mesh column programmed from 150 to 250°C and held at 250°C for at least 10 minutes. Helium flow rate was 50 cc/min. Nuclear magnetic resonance spectra were obtained on a Varian T60 spectrometer. Mass spectra were recorded by a Consolidated Electrodynamics 21-130 mass spectrometer.

The following examples (XXVI–XXIX) are described in detail to assist in establishing the scope of the inventive process.

EXAMPLE XXVI (Method II)

This run was carried out essentially in accordance with the general procedure of Method II with the following charge: 0.50 mol (47.0 g) norbornene, 50 ml n-hexane, 0.53 mol (17.0 g) methanol, and 0.68 mol (102 g, 60 ml) trifluoromethanesulfonic acid. On workup a 53.0 g residue was obtained. Glc analysis of this residue showed no dimer ester type product. Two major components were detected by glc analysis: 2-methoxynorbornane (66.2 area percent) and 2-carbomethoxynorbornane (18.9 area percent). A 52.12 g portion of the above residue was distilled to give a 23.92 g fraction (74°–90°C/40–120 mm), a 9.09 g fraction (67°–68°C/35 mm), and a 7.95 g fraction (82°–84°C/1–20 mm). The 7.95 g fraction was shown to be mostly 2-carbomethoxynorbornane ($C_9H_{14}O_2$) by elemental and molecular weight analysis.

Calculated for $C_9H_{14}O_2$: %C, 70.10; %H, 9.15; Mol. wt. 154. Found %C, 70.68; %H, 9.04; Mol. wt. 154.

The 23.92 g and 9.09 g fractions were combined and a 32.08 g portion was redistilled to give a 20.22 g fraction (57°–58°C/25 mm) with a refractive index of 1.4556. This 20.22 g sample was shown to be mostly 2-methoxynorbornane ($C_8H_{14}O$) by elemental and molecular weight analyses.

Calculated for $C_8H_{14}O$: %C, 76.14; %H, 11.18; Mol. wt. 126. Found: %C, 76.08; %H, 10.70; Mol. wt. 125.

EXAMPLE XXVII (Method I)

A 0.53 mol (17 g) sample of methanol was slowly added to 0.34 mol (51 g, 30 ml) trifluoromethanesulfonic acid in a 300 ml Hastelloy B reactor cooled in an ice salt bath. The reactor was capped and pressured to 1,200 psig with carbon monoxide. During a period of 42 minutes at 22°–25°C, a 0.25 mol (41 g) sample of 1-cyclohexyl cyclohexene was pumped into the stirred (2,000 rpm) reaction mixture. Workup gave a 52.45 g residue after concentration of the ether extract. A glc analysis of this residue showed 99.1 area percent methyl 1-bicyclohexylcarboxylate. A 48.90 g sample was distilled to give a 43.97 g fraction (96°C/1.5 mm) of methyl 1-bicyclohexylcarboxylate which had a refractive index of 1.4862. This run showed that even in the presence of trifluoromethanesulfonic acid 1-cyclohexylcyclohexene gave the Koch type product.

EXAMPLE XXVIII (Method I)

A run similar to that described in Example XXVI was carried out in 75 ml liquid HF and yielded 45.7 g of the Koch type product methyl 1-bicyclohexylcarboxylate (123°C/4 mm, refractive index 1.4865).

EXAMPLE XXIX (Method II)

This run was carried out essentially in accord with the general procedure of Method II with the following charge: 0.53 mol (17 g) methanol, 0.68 mol (102 g, 60 ml) trifluoromethanesulfonic acid, and 0.5 mol (42 g) 2-methylpentene-2. The reactor was capped and pressured to 1,200 psig with carbon monoxide. During a 3-hour reaction period, the temperature varied from 0.8° to 18°C. Workup gave a 47.7 g residue. Glc analysis of this crude product gave six peaks which could be methyl esters and ethers ($C_7$–$C_8$ range), 12 unknown peaks, and three peaks which could be esters. No detailed characterization of the product mixture was carried out.

EXAMPLE XXX (Method II)

Two runs were carried out with propylene and were not worked up for detailed characterization because on preliminary examination of the reaction mixture no ester product appeared to be present.

EXAMPLE XXXI (Method II)

This run was carried out in a manner similar to the run described in Example XXVIII. The charge consisted of 0.5 mol (35 g) 2-methylbutene-2, 0.53 mol (17 g) methanol, and 0.68 mol (60 ml, 102 g) trifluoromethanesulfonic acid. The reactor was capped and pressured to 1.180 psig with CO. During a 3-hour reaction period, the temperature varied from +1° to +20°C and workup gave a 15.5 g residue. Glc analysis of this residue indicated very little formation of ester and the reaction mixture was not further characterized.

I claim:

1. A process for the production of dimer acids and esters which comprises reacting
   a. at least one olefin selected from linear olefins having from 4 to 12 carbon atoms and the cyclic olefin cyclohexene,
   b. at least one polar compound selected from water and alcohols of the formula

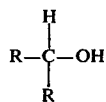

wherein R is hydrogen, alkyl, or hydroxyalkyl with the further proviso that the two R groups together can represent an alkylene grouping selected from tetramethylene and pentamethylene and the total number of carbon atoms does not exceed 12, and
   c. carbon monoxide,
   in the presence of
   d. trifluoromethanesulfonic acid, under reaction conditions including a temperature in the range of about −50°C to about 100°C and carbon monoxide pressure in the range of about 25 to about 5,000 psig to produce dimer acids and esters.

2. A process according to claim 1 wherein the reaction time is in the range of about 5 minutes to about 72 hours, the mole ratio of (a) to (d) is in the range of 0.1 to 3, and the mole ratio of (a) to (b) is in the range of 0.15 to 7.

3. A process according to claim 1 for the production of acids which comprises reacting
   a. at least one olefin as defined,
   b. water, and
   c. carbon monoxide
   in the presence of
   d. trifluoromethanesulfonic acid
   to form acids containing $2n+1$ carbon atoms where n represents the number of carbon atoms in the olefin.

4. A process according to claim 1 for the production of esters wherein (b) is an alcohol or diol as defined having from 1 to 12 carbon atoms to produce acids defined by $[(2n+1) + n']$ wherein n represents the number of carbon atoms in the olefin and $n'$ represents the number of carbon atoms in the alcohol, and when the alcohol is a diol the ester is defined by $[2(2n+1) +n']$ where n and $n'$ are as defined above.

5. A process according to claim 1 wherein the reaction is carried out in a reaction diluent comprising liquid sulfur dioxide or 1,1,2-trichloro-1,2,2-trifluoroethane.

6. A process according to claim 1 for the production of esters of 1-bicyclohexylcarboxylic acid by reacting cyclohexene and carbon monoxide in the presence of trifluoromethanesulfonic acid wherein the alcohol in (b) is methanol, ethanol, 2-propanol, 1-butanol, 1-hexanol, 1-octanol, cyclohexanol, or 1,4-butanediol.

7. A process according to claim 1 for the production of acids of 1-bicyclohexylcarboxylic acids comprising reacting cyclohexene, carbon monoxide and water in the presence of trifluoromethanesulfonic acid.

8. A process according to claim 1 for the production of esters by the reaction of methanol and carbon monoxide in the presence of trifluoromethanesulfonic acid wherein the olefin is 1-butene, cis-2-butene, trans-2-butene, 1-pentene, 2-pentene, 1-hexene, 1-octene, or 1-dodecene.

9. A process according to claim 1 wherein the process is carried out at a reaction temperature in the range of −20°C to 50°C for a period of time in the range of about 30 minutes to about 6 hours under carbon monoxide pressure of about 100 to about 3,000 psig, and further wherein the mole ratio of (a) to (d) is 0.3 to 1.5 and the mole ratio of (b) to (c) is 4 to 2.5.

10. A process according to claim 5 wherein the alcohol is methanol, 1-butanol or 1-hexanol.

* * * * *